United States Patent [19]

Mimura et al.

[11] 4,360,594
[45] Nov. 23, 1982

[54] PROCESS FOR PRODUCING L-TRYPTOPHAN OR DERIVATIVES THEREOF USING MICROORGANISMS

[75] Inventors: Akio Mimura; Yasuyuki Takahashi; Katsumi Yuasa, all of Fuji; Mitsuru Shibukawa, Yokohama, all of Japan

[73] Assignee: Asahi Kasei Kogyo Kabushiki Kaisha, Osaka, Japan

[21] Appl. No.: 274,567

[22] Filed: Jun. 17, 1981

[30] Foreign Application Priority Data

Jun. 17, 1980 [JP] Japan .................................. 55-80917
Jun. 17, 1980 [JP] Japan .................................. 55-80918

[51] Int. Cl.$^3$ ........................ C12P 13/22; C12N 1/20; C12R 1/01; C12R 1/22
[52] U.S. Cl. .................................. 435/108; 435/253; 435/822; 435/852
[58] Field of Search ............................... 435/108, 253

[56] References Cited

U.S. PATENT DOCUMENTS 4,335,209 6/1982 Asai et al. ........................ 435/108

FOREIGN PATENT DOCUMENTS 55-45307 3/1980 Japan .................................. 435/108

OTHER PUBLICATIONS

Nakazawa et al, Agricultural and Biological Chemistry, vol. 36, No. 13, pp. 2523–2528, (1972).
Derwent Abstract 8568c/48 (1980) of Japan 3697 (1980).

Primary Examiner—Lionel M. Shapiro
Attorney, Agent, or Firm—Sughrue, Mion, Zinn, Macpeak & Seas

[57] ABSTRACT

A process for producing L-tryptophan or a derivative thereof is disclosed, wherein an indole compound is reacted with serine, or with pyruvic acid and ammonium ion, in the presence of a culture or treated culture of a microorganism of genus Aeromonas or genus Klebsiella having the ability to produce L-tryptophan or a derivative thereof from an indole compound and serine, or from an indole compound, pyruvic acid and/or its salt, and ammonium ion.

16 Claims, No Drawings

PROCESS FOR PRODUCING L-TRYPTOPHAN OR DERIVATIVES THEREOF USING MICROORGANISMS

FIELD OF THE INVENTION

This invention relates to a process for producing L-tryptophan or derivatives thereof, by using microorgnisms.

BACKGROUND OF THE INVENTION

L-Tryptophan is one of the essential amino acids constituting the bodies of animals, and is important as a medicine, nutrient, or as an additive for animal feed. Some L-tryptophan derivatives work as an antagonist against the metabolism of L-tryptophan and contain physiologically active substances that may be used to prepare pharmaceuticals that affect the central nervous system. These L-tryptophan and its derivatives can be produced by known methods of synthesis, biological process and many other methods. Known methods for producing L-tryptophan using microorganisms include: (1) direct fermentation using sugars to accumulate L-tryptophan in a culture; and (2) adding indole or anthranilic acid simultaneously with sugar to a culture, and permitting L-tryptophan to accumulate in the culture. L-Tryptophan can also be produced from indole and serine or from indole, pyruvic acid and ammonium ion by using a microorganism-produced tryptophanase (enzyme). This method of using tryptophanase has the advantage that by replacing the indole with other indole compounds, various corresponding L-tryptophan derivatives can be produced, and that hence, a reaction that best suits a particular purpose can be selected.

Many methods are known for producing L-tryptophan using tryptophanase. Japanese Patent Publication No. 46917/74 describes a method wherein L-tryptophan is produced from indole and serine or from indole, pyruvic acid and ammonium ion using a microorganism of genus Escherichia, genus Proteus, genus Pseudomonas, genus Aerobacter or genus Erwinia, and French Pat. No. 1,207,437, Japanese patent application (OPI) No. 39693/72 ("OPI" as used herein means an unexamined published Japanese patent application) and Japanese Patent Publication No. 1836/78 describe a method wherein L-tryptophan is produced from indole and serine using a microorganism of genus Escherichia, genus Claviceps, genus Neurospora, genus Saccharomyces, genus Bacillus, genus Achromobacter or genus Alcaligenes. Several methods are also known for producing L-tryptophan derivatives that correspond to various indole compounds: Japanese Patent Publication No. 46917/74 describes a process for producing 5-hydroxytryptophan using a microorganism of genus Proteus, genus Escherichia, genus Pseudomonas, genus Aerobacter or genus Erwinia; Japanese Patent Publication No. 1835/78 describes a method for producing 5-hydroxytryptophan using a microorganism of genus Achromobacter, genus Escherichia, genus Pseudomonas, genus Alcaligenes or genus Proteus; and Japanese Patent Publication Nos. 5479/76 and 8400/77 describe a method for producing 5-hydroxytryptophan and methoxytryptophan using a microorganism of genus Corynebacterium or genus Brevibacterium.

These methods that use microorganisms are advantageous over the method for producing L-tryptophan or its derivatives by chemical synthesis because they provide only L-form compounds that are optically active. They make possible production of large quantities of L-tryptophan or L-tryptophan derivatives from industrial materials such as indole compounds, serine, or pyruvic acid.

SUMMARY OF THE INVENTION

There has now been found new microorganisms that produce L-tryptophan and derivatives thereof in high yield. Using these microorganisms, we have accomplished an invention which is described herein.

This invention provides a process for producing L-tryptophan or a derivative thereof. In the process, an indole compound is reacted with serine, or with pyruvic acid and/or its salt and ammonium ion, in the presence of a culture or treated culture of a microorganism of genus Aeromonas or genus Klebsiella having the ability to produce L-tryptophan or a derivative thereof from an indole compound and serine or from an indole compound, pyruvic acid and/or its salt, and ammonium ion.

DETAILED DESCRIPTION OF THE INVENTION

This invention uses microorganisms of genus Aeromonas or genus Klebsiella that produce L-tryptophan or its derivatives from an indole compound and serine, or from an indole compound, pyruvic acid and/or its salt, and ammonium ion. No microorganism of genus Aeromonas has previously been found to be capable of producing L-tryptophan from indole by the action of tryptophanase (see Agricultural and Biological Chemistry, Vol. 36, p. 2523, 1972).

It is conventionally known that various microorganisms produce tryptophanase, which decomposes L-tryptophan to form indole, but not all microorganisms that produce tryptophanase have the ability to produce a significant amount of L-tryptophan. Microorganisms that produce tryptophanase and which efficiently produce L-tryptophan or a derivative thereof from an indole compound and serine, or from an indole compound, pyruvic acid and/or its salt, and ammonium ion must meet the following requirements: (1) the tryptophanase produded in the microorganisms has high activity; (2) the microorganisms do not decompose the starting materials such as indole compounds, serine, and pyruvic acid; and (3) the microorganisms do not decompose the resulting L-tryptophan or its derivatives other than by the tryptophanase.

According to this invention, a number of tryptophanase-producing microorganisms have been isolated from the soil, including among them new microorganisms of genus Aeromonas and genus Klebsiella that efficiently produce L-tryptophan or its derivatives. Designated Aeromonas SP. AST 108-1, Aeromonas SP. AST 111-4, Klebsiella SP. AST 148-1 and Klebsiella SP. AST 151-7, these microorganisms have been deposited with the Fermentation Research Institute, the Agency of Industrial Science and Technology (FERM) under FERM-P 5539, 5540, 5541 and 5542, respectively, on May 28, 1980, and they are preferred for use in the process of this invention.

Mycological properties of these four microorganisms are listed below.

(I) Aeromonas SP. AST 108-1

(A) Morphological properties (incubation in nutrient broth at 32° C. for 24 hr)

Shape: short rod, single rods or a chain of two rods, a flagellum or flagella located at one end of the bacterium
Size: 0.9–1.2μ × 1.2–2.0μ
Motility: present
Gram-staining: negative
Acid fastness staining: negative
Spores: not formed
Pleomorphism: none (B) Growth in medium (32° C.)
   Nutrient broth: good, no film formed, no ring formed, with precipitate, turbid, no pigment formed
   Nutrient broth agar plate culture: good, circular, smooth surface, raised, entire circular, glossy, slightly Manila paper-colored (i.e., slightly brownish or buff-colored), slightly viscous, no pigment formed
   Nutrient broth agar slant culture: good, filiform, glossy, slightly Manila paper-colored, no pigment formed
   Nutrient broth gelatin stab culture (20° C.): growth good in upper portion, slightly Manila paper-colored, grew a little in stabbed portion, no gas formed in stabbed portion, not liquefied (C) Physiological properties
   Growth temperature: grew at 13°–37° C., did not grow at 45° C.
   Growth pH: 5–9
   Oxygen requirement: facultatively anaerobic
   OF test (Hugh Leifson's medium): fermented
   Gas production (glucose medium): gas produced
   Litmus milk: good growth, slightly Manila paper-colored ring formed, litmus turned to pink, with precipitate, no change in milk
   Liquefaction of gelatin: not liquefied
   Production of hydrogen sulfide: not produced
   Decomposition of starch: not decomposed
   Reduction of nitrate: nitrous acid produced
   Catalase activity: positive
   Oxidase activity: positive
   Urease activity: negative
   Phenylalanine deaminase activity: negative
   Lysine decarboxylase activity: negative
   Alginine dihydrolase activity: positive
   Ornithine decarboxylase activity: positive
   Production of indole: positive
   Production of ammonia: positive
   VP reaction: negative
   MR test: positive
   Denitrification: positive
   Utilization of citric acid:
      Koser medium: utilized
      Christensen medium: utilized
   Sodium chloride fastness: grew in NaCl conc. of up to 5%
   Production of pigment (King A medium): not produced
   Utilization of nitrogen sources: ammonium salt and nitrate utilized
   Utilization of sugars, and production of acid and gas: See Table 1 below.

TABLE 1

| | Growth | Acid production | Gas production |
|---|---|---|---|
| D-glucose | + | + | + |
| D-fructose | + | + | + |
| D-mannose | + | + | + |
| D-galactose | + | + | + |
| D-rhamnose | + | + | + |
| D-arabinose | + | + | + |
| L-arabinose | + | + | + |
| D-xylose | + | + | + |
| Sucrose | + | + | + |
| Lactose | + | − | − |
| Maltose | + | + | + |
| Trehalose | + | + | + |
| Raffinose | + | + | + |
| D-inositol | + | − | − |
| D-mannitol | + | + | + |
| D-adonitol | − | − | − |
| D-dulcitol | − | − | − |
| D-sorbitol | + | + | + |
| Salicin | + | − | − |
| Glycerin | + | + | − |
| Ethanol | − | − | − |

Isolated from: soil of paddy field at Fuji-shi, Shizuoka, Japan (II) Aeromonas SP. AST 111-4

(A) Morphological properties (incubation in nutrient broth at 32° C. for 24 hr)
   Shape: short rod, single rods or a chain of two or three rods, a flagellum or flagella located at one end of the bacterium
   Size: 0.8–1.0μ × 1.2–1.8μ
   Motility: present
   Gram-staining: negative
   Acid fastness staining: negative
   Spores: not formed
   Pleomorphism: none (B) Growth in medium (32° C.)
   Nutrient broth: good, no film formed, ring formed, with precipitate, turbid, no pigment formed
   Nutrient broth agar plate culture: good, circular, smooth surface, raised, entire circular, glossy, grayish white, slightly viscous, no pigment formed
   Nutrient broth agar slant culture: good, slightly liquid, filiform, glossy, grayish white, no pigment formed
   Nutrient broth gelatin stab culture (20° C.): growth good in upper portion, grayish white, grew in stabbed portion, no gas formed in stabbed portion, not liquefied (C) Physiological properties
   Growth temperature: grew at 9°–45° C., did not grow at 50° C.
   Growth pH: 5–10
   Oxygen requirement: facultatively anaerobic
   OF test (Hugh Leifson's medium): fermented
   Gas production (glucose medium): gas produced
   Litmus milk: good growth, litmus decolored, milk coagulated, with precipitate
   Liquefaction of gelatin: not liquefied
   Production of hydrogen sulfide: not produced
   Decomposition of starch: not decomposed
   Reduction of nitrate: nitrous acid produced
   Catalase activity: positive
   Oxidase activity: positive
   Urease activity: positive
   Phenylalanine deaminase activity: negative
   Lysine decarboxylase activity: negative
   Alginine dihydrolase activity: negative
   Ornithine decarboxylase activity: positive
   Production of indole: positive
   Production of ammonia: positive
   VP reaction: positive MR test: negative
Denitrification: positive
Utilization of citric acid:
  Koser medium: utilized
  Christensen medium: utilized
Sodium chloride fastness: grew in NaCl conc. of up to 5%
Production of pigment (King A medium): not produced
Utilization of nitrogen sources: ammonium salt, nitrate and urea utilized
Utilization of sugars, and production of acid and gas: See Table 2 below.

TABLE 2

|  | Growth | Acid production | Gas production |
|---|---|---|---|
| D-glucose | + | + | + |
| D-fructose | + | + | + |
| D-mannose | + | + | + |
| D-galactose | + | + | + |
| D-rhamnose | + | + | + |
| D-arabinose | − | − | − |
| L-arabinose | + | + | + |
| D-xylose | + | + | + |
| Sucrose | + | + | + |
| Lactose | + | + | + |
| Maltose | + | + | + |
| Trehalose | + | + | + |
| Raffinose | + | + | + |
| D-inositol | + | + | + |
| D-mannitol | + | + | + |
| D-adonitol | + | + | + |
| D-dulcitol | − | − | − |
| D-sorbitol | + | + | + |
| Salicin | + | + | + |
| Glycerin | + | + | + |
| Ethanol | + | − | − |

Isolated from: soil of paddy field at Fuji-shi, Shizuoka, Japan

The foregoing are the mycological properties of Aeromonas SP. AST 108-1 and AST 111-4. Identfication by reference to *Bergey's Manual of Determinative Bacteriology*, 8th Ed., 1974, shows the following: the microorganisms belong most reasonably to genus Aeromonas, in family Vibrionaceae, because they are each a Gram-negative bacillus in the form of a short rod, are facultatively anaerobic, have a flagellum or a tuft flagella at one end, are motile, are positive in catalase activity, positive in oxidase activity, and ferment glucose actively to form an acid and gas.

*Bergey's Manual of Determinative Bacteriology*, 8th Ed. describes three microorganisms of genus Aeromonas, viz. *Aeromonas hydrophila, Aeromanas punctata* and *Aeromonas salmonicida. Aeromonas salmonicida* differs from Aeromonas SP. AST 108-1 and AST 111-4 of this invention, because *Aeromonas salmonicida* cannot grow at 37° C. whereas the microorganisms of this invention grow well at that temperature, and *Aeromonas hydrophila* and *Aeromonas punctata* differ from the microorganisms of this invention in many taxonomical properties as listed in Table 3 below. Therefore, the three microorganisms of genus Aeromonas described in Bergey's Manual differ from the new microorganisms of this invention, Aeromonas SP. AST 108-1 and Aeromonas SP. AST 111-4.

TABLE 3

| Taxonomical properties | Aeromonas hydrophila | | | Aeromonas punctata | | AST-108-1 | AST-111-4 |
|---|---|---|---|---|---|---|---|
|  | Hydrophila | Aerogenes | Proteolytica | Punctata | Caviae | | |
| Liquefaction of gelatin | + | + | + | + | + | − | − |
| Production of hydrogen sulfide | + | + | − | + | + | − | − |
| Lysine decarboxylase activity | − | − | + | − | − | − | − |
| VP reaction | +~−* | +~−* | + | − | − | − | − |
| Resistance to 7.5% NaCl | − | − | + | − | − | − | − |
| Production of gas from glycerin | + | − | − | − | − | − | + |
| Production of gas from glucose | + | − | − | + | − | + | + |

*+~−: Species include various strains, some being "+" and some "−".

(III) Klebsiella SP. AST 148-1
(A) Morphological properties (incubation in nutrient broth at 32° C. for 24 hour)
  Shape: short rod, a single rod or a chain of 2 or 3 rods, no flagella
  Size: $1.1–1.3\mu \times 1.8–2.0\mu$
  Motility: absent
  Gram-staining: negative
  Acid fastness staining: negative
  Spores: not formed
  Pleomorphism: none
(B) Growth in medium (32° C.)
  Nutrient broth: good, no film formed, ring formed, with precipitate, turbid, no pigment formed
  Nutrient broth agar plate culture: good, circular, smooth surface, raised, entire circular glossy, grayish white, somewhat viscous, no pigment formed
  Nutrient broth agar slant culture: good, filiform, glossy, grayish white, no pigment formed
  Nutrient broth gelatin stab culture (20° C.): growth good in upper portion, grayish white, grew in stabbed portion, no gas formed in stabbed portion, not liquefied
(C) Physiological properties
  Growth temperature: grew at 9°–42° C., did not grow at 45° C.
  Growth pH: 4–9
  Oxygen requirement: facultatively anaerobic
  OF test (Hugh Leifson's medium): fermented
  Gas production (glucose medium): gas produced
  Litmus milk: good growth, litmus decolored, milk coagulated, precipitated, not peptonized
  Liquefaction of gelatin: not liquefied
  Production of hydrogen sulfide: not produced
  Decomposition of starch: not decomposed
  Reduction of nitrate: nitrous acid formed
  Catalase activity: positive
  Oxidase activity: negative
  Urease activity: positive
  Phenylalanine deaminase activity: negative
  Lysine decarboxylase activity: positive
  Alginine dihydrolase activity: negative Ornithine decarboxylase activity: negative
Indole production: positive
Ammonia production: positive
VP reaction: positive
MR test: negative
Denitrification: positive
Utilization of citric acid:
  Koser medium: utilized
  Christensen medium: utilized
Sodium chloride fastness: grew in NaCl conc. of up to 4%
Production of pigment (King A medium): not produced
Utilization of nitrogen sources: ammonium salt, nitrate and urea utilized
Utilization of sugars, and production of acid and gas: See Table 4.

TABLE 4

|  | Growth | Acid production | Gas production |
|---|---|---|---|
| D-glucose | + | + | + |
| D-fructose | + | + | + |
| D-mannose | + | + | + |
| D-galactose | + | + | + |
| D-rhamnose | + | + | + |
| D-arabinose | + | + | + |
| L-arabinose | + | + | + |
| D-xylose | + | + | + |
| Sucrose | + | + | + |
| Lactose | + | + | + |
| Maltose | + | + | + |
| Trehalose | + | + | + |
| Raffinose | + | + | + |
| D-inositol | + | + | + |
| D-mannitol | + | + | + |
| D-adonitol | + | + | + |
| D-dulcitol | + | + | + |
| D-sorbitol | + | + | + |
| Salicin | + | + | + |
| Glycerin | + | + | + |
| Ethanol | + | − | − |

Isolated from: soil of paddy field at Fuji-shi, Shizuoka, Japan (IV) Klebsiella SP. AST 151-7

(A) Morphological properties (incubation in nutrient broth at 32° C. for 24 hour)
  Shape: short rod, a single rod or a chain of 2 or 3 rods, no flagella
  Size: $1.0$-$1.2\mu \times 2.2$-$3.0\mu$
  Motility: absent
  Gram-staining: negative
  Acid fastness staining: negative
  Spores: not formed
  Pleomorphism: none
(B) Growth in medium (32° C.)
  Nutrient broth: good, no film formed, grayish white ring formed, precipitated, turbid, no pigment formed
  Nutrient broth agar plate culture: good, circular, smooth surface, raised, entire circular, glossy, grayish white, slightly viscous, no pigment formed
  Nutrient broth agar slant culture: good, slightly undulate, filiform, glossy, grayish white, no pigment formed
  Nutrient broth gelatin stab culture (20° C.): growth good in upper portion, grayish white, grew slightly in stabbed portion, no gas formed in stabbed portion, not liquefied
(C) Physiological properties
  Growth temperature: grew at 13°-42° C., did not grow at 45° C.
  Growth pH: 5-9
  Oxygen requirement: facultatively anaerobic
  OF test (Hugh Leifson's medium): fermented
  Gas production (glucose medium): gas produced
  Litmus milk: good growth, litmus decolored, milk coagulated, precipitated, not peptonized
  Liquefaction of gelatin: not liquefied
  Production of hydrogen sulfide: not produced
  Decomposition of starch: not decomposed
  Reduction of nitrate: nitrous acid produced
  Catalase activity: positive
  Oxidase activity: negative
  Urease activity: positive
  Phenylalanine deaminase activity: negative
  Lysine decarboxylase activity: positive
  Alginine dihydrolase activity: negative
  Ornithine decarboxylase activity: negative
  Indole production: positive
  Ammonia production: positive
  VP reaction: positive
  MR test: positive
  Denitrification: positive
  Utilization of citric acid:
    Koser medium: utilized
    Christensen medium: utilized
  Sodium chloride fastness: grew in NaCl conc. of up to 4%
  Formation of pigment (King A medium): not formed
  Utilization of nitrogen sources: ammonium salt, nitrate and urea utilized
  Utilization of sugars, and production of acid and gas: See Table 5.

TABLE 5

|  | Growth | Acid production | Gas production |
|---|---|---|---|
| D-glucose | + | + | + |
| D-fructose | + | + | + |
| D-mannose | + | + | + |
| D-galactose | + | + | + |
| D-rhamnose | + | + | + |
| D-arabinose | − | − | − |
| L-arabinose | + | + | + |
| D-xylose | + | + | + |
| Sucrose | + | + | + |
| Lactose | + | + | + |
| Maltose | + | + | + |
| Trehalose | + | + | + |
| Raffinose | + | + | + |
| D-inositol | + | + | + |
| D-mannitol | + | + | + |
| D-adonitol | + | + | + |
| D-dulcitol | − | − | − |
| D-sorbitol | + | + | + |
| Salicin | + | + | + |
| Glycerin | + | + | + |
| Ethanol | + | − | − |

Isolated from: soil of paddy field at Fuji-shi, Shizuoka, Japan

These are the mycological properties of Klebsiella SP. AST 148-1 and AST 151-7 according to this invention. Identification by reference to *Bergey's Manual of Determinative Bacteriology*, 8th Ed., 1974, shows the following: the microorganisms belong to family Enterobacteriaceae because they are a Gram-negative bacillus, are facultatively anaerobic, are positive in catalase activity, negative in oxidase activity, produce an acid from glucose and reduce nitric acid to nitrous acid, and they both belong most reasonably to genus Klebsiella in tribe Klebsiella since they are positive in VP reaction, negative in phenylalanine deaminase activity, negative in production of hydrogen sulfide, positive in lysine decarboxylase activity, negative in ornithine decarboxylase activity, negative in alginine dihydrolase activity, and are nonmotile.

No microorganism of genus Klebsiella has been known to produce L-tryptophan from indole, pyruvic acid, and ammonium ion. Table 6 compares the mycological properties of Klebsiella SP. AST 148-1 and AST 151-7 with those of three bacteria of genus Klebsiella described in Bergey's Manual of Determinative Bacteriology, 8th Ed.

TABLE 6

| | Microorganism | | | | |
|---|---|---|---|---|---|
| Taxonomical properties | AST 148-1 | AST 151-7 | Klebsiella pneumoniae | Klebsiella ozaenae | Klebsiella rhinoscleromatis |
| VP reaction | + | + | + | − | − |
| MR test | − | − | − | + | + |
| Indole production | + | + | − | − | − |
| Urease activity | + | + | + | +~−* | − |
| Lysine decarboxylase activity | + | + | + | +~−* | − |
| Alginine dihydrolase activity | − | − | − | − | − |
| Ornithine decarboxylase activity | − | − | − | − | − |
| Utilization of citric acid | + | + | + | +~−* | − |
| Utilization of malonic acid | + | + | + | − | + |
| Gas production | | | | | |
| glucose | + | + | + | +~−* | − |
| glycerin | + | + | − | +~−* | − |
| Acid production | | | | | |
| lactose | + | + | + | + | − |
| dulcitol | + | − | +~−* | − | − |

*+ ~ −: See Table 3

Based on this taxonomical data, it can be concluded that Klebsiella SP. AST 148-1 and AST 151-7 are microorganisms that differ from the three microorganisms of genus Klebsiella that are described in Bergey's Manual of Determinative Bacteriology, 8th Ed.

This invention relates to a new process for producing L-tryptophan and its derivatives by using Aeromonas SP. AST 108-1, Aeromonas SP. AST 111-4, Klebsiella SP. AST 148-1 and Klebsiella SP. AST 151-7 described above. The microorganisms can be cultured on a common synthetic or natural medium. Carbon sources include sugars such as glucose, fructose, mannose, sucrose, galactose, xylose, and molasses; sugar alcohols such as glycerin, and sorbitol; and organic acids such as acetic acid, citric acid, fumaric acid, malic acid and succinic acid. These carbon sources are added to a medium generally in an amount of from about 0.1% to 10% by weight. Nitrogen sources include ammonias such as ammonium chloride, ammonium phosphate, ammonium nitrate, ammonium acetate and ammonia water; and organic nitrogen sources such as urea, meat extract, peptone, Casamino acid, corn steep liquor, defatted soybean meal, and protein hydrolyzate. Substances that promote the growth of the microorganisms used are preferably added to the medium. The substance may be inorganic or organic. Inorganic examples include potassium monophosphate, potassium diphosphate, phosphoric acid, potassium chloride, magnesium sulfate and sodium chloride, as well as metal ions such as iron, zinc, manganese, copper and calcium. Organic examples include amino acids, vitamins, organic acids, aliphatic acids, as well as natural substances such as peptone, yeast extract, dried yeast, corn steep liquor, casein and defatted soybean hydrolyzate.

Tryptophanase produced by the microorganisms used in this invention is considered an adaptive enzyme, and L-tryptophan is preferably added to the medium for preparing a culture of the microorganism in an amount of from about 0.1% to 0.7% by weight. The microorganisms are incubated in the resulting medium at from 25° C. to 37° C. for from 16 to 96 hours.

The thus-prepared culture of the microorganisms has an enzyme system that produces L-tryptophan or its derivatives from an indole compound and serine or from an indole compound, pyruvic acid and/or its salt, and ammonium ion. The culture may be immediately used in the desired enzymatic reaction, or it may be used after suitable preliminary treatments. For example, the microorganism cells may be separated from the culture by centrifugation or the like. The cells may also be dried, treated with ultrasonic waves, autolyzed or homogenized. Instead, the produced tryptophanase produced may be extracted and purified by conventional manner. Alternatively, the separated cells or enzyme may be used as immobilized cells or enzyme obtained by polymerizing them with an acrylic acid amide monomer or the like.

The thus-prepared tryptophanase-containing cells, treated cells and immobilized cells, as well as the purified tryptophanase and the immobilized tryptophanase are used as a catalyst for enzymatic reaction in a reaction liquor comprising an indole compound and serine, or an indole compound, pyruvic acid and/or its salt, and ammonium ion for production of L-tryptophan or its derivatives. In addition to the indole compound, serine, pyruvic acid and/or its salt, and ammonium ion used as substrate, the reaction liquor preferably contains ethylenediaminetetraacetic acid and pyridoxal phosphate for achieving a higher yield of L-tryptophan or derivatives thereof. There is no particular limitation on the amount of the substrate used, and generally it is in the range of from 0.1% to 10% by weight. The enzymatic reaction is usually performed at a pH in the range of from 5 to 11 and at a temperature in the range of from 10° to 60° C. Examples of the indole compound to be added to the reaction system include indole, 5-hydroxyindole, 5-chloroindole, 5-bromoindole, 5-aminoindole, 5-methoxyindole, 5-methoxy-2-methylindole, and 2-methylindole.

The L-tryptophan or its derivatives produced in the reaction liquor can be isolated by conventional methods including adsorption with ion exchange resin, activated carbon, etc. The L-tryptophan and derivatives thereof produced can be verified and quantified by high-pressure liquid chromatography or silica gel thin-layer chromatography.

This invention is now described in greater detail by reference to the following examples which are given here for illustrative purposes only, and are not intended to limit the scope of the invention.

EXAMPLE 1

Five milliliters of a medium having the formulation indicated in Table 7 was charged into test tubes having a diameter of 18 mm and sterilized at 120° C. for 10 minutes. Each of the sterilized media was inoculated with one loopful of Aeromonas SP. AST 108-1, and cultivated at 32° C. for 20 hours under shaking. Five milliliters of the thus germinated culture was transferred to a fermentation medium prepared by sterilizing 100 ml of a medium (the same as indicated in Table 7) at 120° C. for 10 minutes in a 500-ml shake flask, and fermentation was conducted at 32° C. for 20 hours under shaking. After completion of the fermentation, two liter of the culture was centrifuged to recover the microorganism cells, and the cells were suspended in 180 ml of a reaction liquor having a pH of 9.0 and consisting of 2 g of sodium pyruvate, 2 g of ammonium acetate, 10 mg of pyridoxal phosphate, 200 mg of ethylenediaminetetraacetic acid and 100 ml of water. The suspension was divided into six equal amounts. 30 ml of each suspension was mixed with 600 mg of the indole compounds indicated in Table 8, and each mixture was heated at 32° C. for 72 hours under shaking to effect an enzymatic reaction. After completion of the reaction, 30 ml of methanol was added to each reaction mixture under vigorous stirring, and the mixture was centrifuged. The resulting supernatant was subjected to high-pressure liquid chromatography; L-tryptophan derivatives corresponded to the indole compounds used were produced in the amounts indicated in Table 8.

TABLE 7

| | |
|---|---|
| Peptone | 2% by weight |
| Casamino acids | 1 |
| Yeast extract | 0.5 |
| Corn steep liquor | 5 |
| L-Tryptophan | 0.2 |
| $KH_2PO_4$ | 0.05 |
| $MgSO_4.7H_2O$ | 0.05 |
| $FeSO_4.7H_2O$ | 0.003 |
| $MnSO_4.4H_2O$ | 0.003 |
| pH | 7.2 |

TABLE 8

| Indole compound | L-tryptophan derivatives produced | Amount (g/l) |
|---|---|---|
| Indole | L-Tryptophan | 10.3 |
| 5-Hydroxyindole | 5-Hydroxytryptophan | 2.9 |
| 5-Chloroindole | 5-Chlorotryptophan | 0.9 |
| 5-Bromoindole | 5-Bromotryptophan | 0.7 |
| 5-Aminoindole | 5-Aminotryptophan | 1.1 |
| 5-Methoxyindole | 5-Methoxytryptophan | 0.6 |

To the reaction product obtained by using indole, caustic soda was added to bring its pH to 10, and the mixture was passed through a column of ammonia type strongly acidic ion exchange resin and the adsorbed L-tryptophan was eluted with 2 N ammonia water. The eluate was concentrated to form a crude L-tryptophan crystal which was washed with acetone and dried to give 185 mg of an L-tryptophan crystal.

EXAMPLE 2

Aeromonas SP. AST 108-1 was fermented as in Example 1 to obtain two liters of a culture. The culture was centrifuged to recover the microorganism cells, and the cells were suspended in 180 ml of a reaction liquor having a pH of 9.0 and consisting of 1.5 g of L-serine, 10 mg of pyridoxal phosphate, 200 mg of ethylenediaminetetraacetic acid and 100 ml of water. The suspension was divided into six equal amounts. 30 ml of each suspension was mixed with 600 mg of the indole compounds indicated in Table 9, and each mixture was heated at 32° C. for 72 hours under shaking to effect an enzymatic reaction. After completion of the reaction, the reaction products were treated as in Example 1 and subjected to high-pressure liquid chromatography; L-tryptophan derivatives corresponded to the indole compounds used were produced in the amount indicated in Table 9.

TABLE 9

| Indole compound | L-tryptophan derivatives produced | Amount (g/l) |
|---|---|---|
| Indole | L-Tryptophan | 11.8 |
| 5-Hydroxyindole | 5-Hydroxytryptophan | 2.5 |
| 5-Chloroindole | 5-Chlorotryptophan | 1.1 |
| 5-Bromoindole | 5-Bromotryptophan | 1.3 |
| 5-Aminoindole | 5-Aminotryptophan | 1.2 |
| 5-Methoxyindole | 5-Methoxytryptophan | 0.8 |

EXAMPLE 3

Aeromonas SP. AST 111-4 was fermented as in Example 1 to obtain four liters of a culture. The culture was centrifuged to recover the microorganism cells one half of which were suspended in 180 ml of a reaction liquor having a pH of 9.0 and consisting of 2 g of sodium pyruvate, 2 g of ammonium acetate, 10 mg of pyridoxal phosphate, 200 mg of ethylenediaminetetraacetic acid and 100 ml of water. The other half was suspended in 180 ml of a reaction liquor having a pH of 9.0 and consisting of 1.5 g of L-serine, 10 mg of pyridoxal phosphate, 200 mg of ethylenediaminetetraacetic acid and 100 ml of water. Each reaction liquor was divided into six equal amounts as in Examples 1 and 2 and mixed with 600 mg of the indole compounds indicated in Table 10, and each mixture was heated at 32° C. for 72 hours under shaking to effect an enzymatic reaction. After completion of the reaction, the reaction products were treated as in Example 1 and subjected to high-pressure liquid chromatography; L-tryptophan derivatives corresponded to the indole compounds used were produced in the amounts indicated in Table 10.

TABLE 10

| | Amount of L-tryptophan derivatives produced (g/l) | |
|---|---|---|
| Indole compound | Pyruvate-containing system | L-serine-containing system |
| Indole | 14.4 | 17.2 |
| 5-Hydroxyindole | 1.9 | 2.4 |
| 5-Chloroindole | 1.1 | 1.4 |
| 5-Bromoindole | 1.0 | 1.0 |
| 5-Aminoindole | 1.5 | 1.6 |
| 5-Methoxyindole | 1.2 | 1.5 |

EXAMPLE 4

Five milliliters of a medium having the formulation indicated in Table 7 was charged into test tubes having a diameter of 18 mm and sterilized at 120° C. for 10 minutes. Each of the sterilized media was inoculated with one loopful of the microorganisms indicated in Table 11, and cultivated at 32° C. for 20 hours under shaking. Five milliliters of each germinated culture was transferred to a fermentation medium prepared by sterilizing 100 ml of a medium (the same as indicated in Table 7) at 120° C. for 10 minutes in a 500-ml shake flask, and fermentation was conducted at 32° C. for 20 hours under shaking. After completion of the fermentation, one liter of the culture was centrifuged to recover the cells of each microorganism, and the cells were suspended in 200 ml of a reaction liquor having the formulation indicated in Table 12, and each suspension was heated at 32° C. for 48 hours under shaking to effect an enzymatic reaction. After completion of the reaction, 10 ml of the suspension was mixed with 10 ml of methanol under vigorous stirring, and the mixture was centrifuged. Analysis of the resulting supernatant by high-pressure liquid chromatography showed that L-tryptophan was produced in the reaction liquors in the amounts indicated in Table 11.

TABLE 11

| Microorganism | L-tryptophan produced (g/l) |
|---|---|
| Klebsiella SP. AST 148-1 | 11.2 |
| Klebsiella SP. AST 151-7 | 13.4 |

TABLE 12

| | |
|---|---|
| Indole | 20 g |
| Sodium pyruvate | 20 g |
| Ammonium acetate | 20 g |
| Pyridoxal phosphate | 100 mg |
| Ethylenediaminetetra-acetic acid | 2 g |
| Water | 1 liter |
| pH | 9.0 |

EXAMPLE 5

As in Example 4, the microorganisms indicated in Table 13 were fermented on a medium having the formulation indicated in Table 7. One liter of each culture was centrifuged to recover the cells of each microorganism and they were suspended in 200 ml of a reaction liquor having a pH of 9.0 and consisting of 2 g of indole, 3 g of L-serine, 10 mg of pyridoxal phosphate, 200 mg of ethylenediaminetetraacetic acid and 100 ml of water. Each suspension was heated at 32° C. for 36 hours under shaking to effect an enzymatic reaction. After completion of the reaction, 10 ml of the suspension was mixed with 10 ml of methanol under vigorous stirring, and the mixture was centrifuged. Analysis of the resulting supernatant by high-pressure liquid chromatography showed that L-tryptophan was produced in the reaction liquors in the amounts indicated in Table 13.

TABLE 13

| Microorganism | L-tryptophan produced (g/l) |
|---|---|
| Klebsiella SP. AST 148-1 | 15.4 |
| Klebsiella SP. AST 151-7 | 16.2 |

EXAMPLE 6

As in Example 4, Klebsiella SP. AST 151-7 was fermented on a medium having the formulation indicated in Table 7. Four liters of the culture was centrifuged to recover the microorganism cells. One half of the cells was suspended in a reaction liquor containing sodium pyruvate and ammonium acetate as in Example 4, and was mixed with the indole compounds indicated in Table 14. The other half of the cells was suspended in a reaction liquor containing L-serine as in Example 5 and was mixed with the indole compounds indicated in Table 14. Each mixture was then subjected to an enzymatic reaction at 32° C. for 72 hours under shaking. After completion of the reaction, the reaction mixture was subjected to highpressure liquid chromatograph; L-tryptophan derivatives corresponding to the indole compounds used were produced in the amounts indicated in Table 14.

TABLE 14

| | Amount of L-tryptophan derivatives produced (g/l) | |
|---|---|---|
| Indole compound | Pyruvate-containing system | L-serine-containing system |
| 5-Hydroxyindole | 1.8 | 2.4 |
| 5-Chloroindole | 1.1 | 1.3 |
| 5-Bromoindole | 1.2 | 1.3 |
| 5-Aminoindole | 0.9 | 1.2 |
| 5-Methoxyindole | 0.8 | 1.0 |
| 5-Methoxy-2-methylindole | 0.9 | 0.9 |
| 2-Methylindole | 1.3 | 1.4 |

While the invention has been described in detail and with reference to specific embodiments thereof, it will be apparent to one skilled in the art that various changes and modifications can be made therein without departing from the spirit and scope thereof.

What is claimed is:

1. A process for producing L-tryptophan or a derivative thereof, wherein an indole compound is reacted with serine, or with pyruvic acid and/or its salt and ammonium ion, in the presence of a culture or treated culture of a microorganism of genus Aeromonas or genus Klebsiella having the ability to produce L-tryptophan or a derivative thereof from an indole compound and serine, or from an indole compound, pyruvic acid and/or its salt, and ammonium ion, said microorganism of genus Klebsiella being selected from the group consisting of Klebsiella SP. AST 148-1 having the FERM designation FERM-P 5541 and Klebsiella SP. AST 151-7 having the FERM designation FERM-P 5542.

2. A process according to claim 1, wherein the microorganism is of the genus Aeromonas.

3. A process according to claim 1, wherein the microorganism is of the genus Klebsiella.

4. A process according to claim 1 wherein the indole compound is selected from the group consisting of indole, 5-hydroxyindole, 5-chloroindole, 5-bromoindole, 5-aminoindole, 5-methoxyindole, 5-methoxy-2-methylindole, and 2-methylindole.

5. A process according to claim 1 wherein the microorganism is selected from the group consisting of Aeromonas SP. AST 108-1 having the FERM designation FERM-P 5539, Aeromonas SP. AST 111-4 having the FERM designation FERM-P 5540, Klebsiella SP. AST 148-1 having the FERM designation FERM-P 5541, and Klebsiella SP. AST 151-7 having the FERM designation FERM-P 5542.

6. A process according to claim 4, wherein the microorganism is selected from the group consisting of Aeromonas SP. AST 108-1 having the FERM designation FERM-P 5539, Aeromonas SP. AST 111-4 having the FERM designation FERM-P 5540, Klebsiella SP. AST 148-1 having the FERM designation FERM-P 5541, and Klebsiella SP. AST 151-7 having the FERM designation FERM-P 5542.

7. A process according to claim 6, wherein the microorganism is Aeromonas SP. AST 108-1 having the FERM designation FERM-P 5539.

8. A process according to claim 6, wherein the microorganism is Aeromonas SP. AST 111-4 having the FERM designation FERM-P 5540.

9. A process according to claim 6, wherein the microorganism is Klebsiella SP. AST 148-1 having the FERM designation FERM-P 5541.

10. A process according to claim 6, wherein the microorganism is Klebsiella SP. AST 151-7 having the FERM designation FERM-P 5542.

11. A process according to claim 1, 2 or 3, wherein the reaction is carried out at a temperature of from 25° C. to 37° C. for from 16 to 96 hours.

12. A process according to claim 4, wherein the reaction is carried out at a temperature of from 25° C. to 37° C. for from 16 to 96 hours.

13. A biologically pure culture of Aeromonas SP. AST 108-1 having the FERM designation FERM-P 5539, having the ability to produce L-tryptophan or a derivative thereof from an indole compound and serine, or from an indole compound, pyruvic acid and/or its salt, and ammonium ion by utilizing assimilable source of carbon, nitrogen and organic or inorganic substances that promote the growth of the culture.

14. A biologically pure culture of Aeromonas SP. AST 111-4 having the FERM designation FERM-P 5540, having the ability to produce L-tryptophan or a derivative thereof from an indole compound and serine, or from an indole compound, pyruvic acid and/or its salt, and ammonium ion, by utilizing assimilable sources of carbon, nitrogen, and organic or inorganic substances that promote the growth of the culture.

15. A biologically pure culture of Klebsiella SP. AST 148-1 having the FERM designation FERM-P 5541, having the ability to produce L-tryptophan or a derivative thereof from an indole compound and serine, or from an indole compound, pyruvic acid and/or its salt and ammonium ion, by utilizing assimilable source of carbon, nitrogen and organic or inorganic substances that promote the growth of the culture.

16. A biologically pure culture of Klebsiella SP. AST 151-7 having the FERM designation FERM-P 5542, having the ability to produce L-tryptophan or a derivative thereof from an indole compound and serine, or from an indole compound, pyruvic acid and/or its salt, and ammonium ion by utilizing assimilable source of carbon, nitrogen and organic or inorganic substances that promote the growth of the culture.

* * * * *